US006811314B2

(12) United States Patent
Cresens

(10) Patent No.: US 6,811,314 B2
(45) Date of Patent: Nov. 2, 2004

(54) EDGE PHANTOM

(75) Inventor: Marc Cresens, Diest (BE)

(73) Assignee: AGFA-Gevaert, Mortsel (BE)

( * ) Notice: Subject to any disclaimer, the term of this patent is extended or adjusted under 35 U.S.C. 154(b) by 0 days.

(21) Appl. No.: 10/441,675

(22) Filed: May 20, 2003

(65) Prior Publication Data

US 2003/0227999 A1 Dec. 11, 2003

Related U.S. Application Data

(60) Provisional application No. 60/389,348, filed on Jun. 17, 2002.

(30) Foreign Application Priority Data

Jun. 5, 2002 (EP) .............................. 02100669

(51) Int. Cl.[7] .............................. G01D 18/00
(52) U.S. Cl. ...................... 378/207; 378/18
(58) Field of Search ................... 378/207, 18

(56) References Cited

U.S. PATENT DOCUMENTS

| 4,352,020 | A | | 9/1982 | Horiba et al. ............... 378/18 |
| 4,980,904 | A | | 12/1990 | Sones et al. ............... 378/207 |
| 5,083,920 | A | * | 1/1992 | Molteni et al. ............... 433/72 |
| 6,488,409 | B1 | * | 12/2002 | Vafi et al. ............... 378/207 |

FOREIGN PATENT DOCUMENTS

| EP | 0 659 386 A1 | 6/1995 |
| EP | 1 062 912 A1 | 12/2000 |
| EP | 02 10 0669 | 11/2002 |

* cited by examiner

Primary Examiner—Craig E. Church
Assistant Examiner—Jurie Yun
(74) Attorney, Agent, or Firm—John A. Merecki; Hoffman, Warnick & D'Alessandro

(57) ABSTRACT

An edge phantom for assessing the sharpness response of a radiation image recording and detection system wherein the edge phantom is subjected to radiation emitted by a source of radiation to generate a radiation image and wherein the radiation image, recorded and detected by the system, is evaluated. The design of the edge phantom provides that any line outside a plane perpendicular to the edge phantom's top face, connecting the focus of the source of radiation with a point on a curved or flat lateral face of the phantom used for sharpness analysis coincides with a line part of that lateral face containing that point.

10 Claims, 3 Drawing Sheets

EDGE PHANTOM

This application claims benefit of Provisional No. 60/389,348 filed Jun. 17, 2002.

FIELD OF THE INVENTION

The present invention relates to image quality performance measurement of digital radiography systems. The invention more particularly relates to a phantom for assessing the edge-step response based sharpness of a digital radiography system.

BACKGROUND OF THE INVENTION

In the field of digital radiography image quality performance measurement tools have been developed that consist of measuring or assessing image quality characteristics of radiation images of test phantoms.

A particular example of an image quality measurement is the assessment of the sharpness of a digital radiography system such as a system in which a radiographic image is temporarily recorded on a photo-stimulate phosphor screen. In such a system the image stored in the screen is read by scanning the screen with stimulating radiation and by converting the light emitted upon stimulation into a digital representation of the image.

For the purpose of assessing the sharpness of a digital radiography system, the edge response of the system is evaluated. Hereto so-called edge phantoms (also called 'edge device') have been developed.

An edge phantom is an object that renders an image corresponding with a step response when it is irradiated e.g. By means of a beam of radiation such as an X-ray beam.

In Medical Physics, Vol. 25, No.1, January 1998 Samei et al. report on measuring pre-sampled modulation transfer function (MTF) of a digital radiographic system.

An edge phantom device is placed in an X-ray beam so that the X-rays modulated by the edge device are recorded on a photo-stimulate phosphor screen. The edge is oriented either horizontally or vertically depending on the direction along which the MTF is being measured.

Also in Proceedings of SPIE vol. 4320 (2001), p. 308–315 a method has been described for testing the image quality of digital radiography system, more specifically a photo-stimulate phosphor based digital radiography system.

A test phantom has been described consisting of a 1,0 mm thick Cu plate into which a series of square holes are cut. One of the square holes is used for pre-sampling modulation transfer function (MTF) measurements in both fast scan (laser scan) and slow scan (screen transport direction).

A phantom image was acquired under well-controlled exposure conditions. MTF was calculated for slow scan and fast scan directions from the edge response functions derived from the edges of one of the square holes cut out of the phantom.

The state of the art phantom design and mode of operation have the following drawbacks.

The phantom is exposed to an amount of radiation emitted by an X-ray source. Because the X-ray source has a substantially point-like behaviour, the direct beams of radiation emitted by this source that reach the phantom are diverging.

If the edge phantom is centered in a plane which is perpendicular to the optical axis of the X-ray source, semi-shadows will originate at the edges of the phantom, the part of the phantom used for MTF or DQE measurements, at a non-zero distance from the optical axis of the X-ray source. These shadows are a consequence of the divergence of the radiation, the thickness of the piece of absorbing material which is not negligible and the fact that the edges are perpendicular to the absorber's top and bottom faces. The fact that the lateral faces of the phantom are straight and vertical has an influence on the slope of the analyzed image signal in the immediate, close surrounding of the lateral face. The calculated MTF value will thus always give an erroneous measure of the actual sharpness of the imaging system.

It is an object of the present invention to provide a measurement phantom suitable for sharpness analysis on digital X-ray systems.

It is a further object to provide such a phantom wherein the influence of the phantom edges to the analyzed sharpness is substantially neutralized when the absorber is located in its nominal position relative to the radiation source.

SUMMARY OF THE INVENTION

The above-mentioned objects are realized by an edge phantom as set out in claim 1.

Another aspect of this invention relates to a method of assessing the sharpness of a radiation image recording and detection system as set out in claim 3.

Specific embodiments are set out in the dependent claims.

As will be explained further on, the present invention is advantageous in that the phantom permits the simultaneous assessment of the sharpness of the system in multiple, spatial directions based on step response information from spatially distributed image areas using only a single radiation exposure.

Furthermore the phantom provides an optimal knife edge radiation input to the system independent of the nominal position of the phantom edges relative to the cone of radiation. Rays impinging on the detector will either be attenuated during their transit through the absorber's full thickness or will pass un-attenuated. Semi-shadow effects at the absorber's edges due to reduced attenuation during passage through a shorter absorber material trajectory are fully cancelled by design.

In the context of the present invention an edge phantom is a phantom that is suitable for assessing the sharpness of a radiation image recording and detection system. The edge-like, spatial step-response of the system resulting from a sudden change in irradiation level, invoked by the phantom, along a given spatial direction can be used to calculate the modulation transfer function (MTF) in that analysis direction.

The evaluation procedure is commonly as follows: an edge phantom is irradiated by an amount of radiation emitted by a source of radiation and the radiation modulated by the edge phantom is recorded and detected by the system. A digital data set representing the radiation image of the phantom is generated. The step response of the radiation image recording and detection system can then be assessed by evaluating the digital image representation.

In the context of the present invention the radiation is commonly radiation by means of X-rays. However, other forms of penetrating radiation are possible.

By means of the terms 'focus of the source of radiation' is meant a point in the source of radiation from which all emitted radiation originates.

By means of the terms 'top face' is meant the face of the phantom the X-rays impinge upon (i.e. tube side).

An example of radiation image recording and detection system is a digital radiography system based on storage phosphor technology. In such as a system a radiation image of an object is recorded on a photo-stimulate phosphor screen. The detection of the image comprises scanning the exposed screen carrying the radiation image by means of light having a wavelength(s) in the stimulating wavelength range of the phosphor and detecting image-wise modulated light emitted by the phosphor upon stimulation. The detection further comprises the step of converting the image-wise modulated light into a digital signal representative of the radiation image.

Another example of a radiation image recording and detection system is a direct radiography system wherein a radiation image is recorded on a radiation to signal converter which immediately converts the image-wise modulated radiation into a digital signal representative of the radiation image.

Still alternative systems may be envisaged.

From the generated digital image the edge response can be measured and several quantities such as MTF or DQE can be calculated for example by applying state of the art methods such as the method described in Proceedings of SPIE, Vol. 4320 (2001), p. 308–315.

A phantom according to the present invention generally comprises a three-dimensional piece of radiation absorbing material, for example in the case of X-rays the piece may be composed of copper. The piece of material either has beveled edge planes (edge planes refer to lateral faces of the piece of radiation absorbing material) or has a cut-away the edge planes of which are beveled.

In general, for edge phantoms having curved lateral faces (also called side walls) the focus point of the source of radiation must be part of any straight line lying in the curved side wall surface. In other words the curved surface should be straight in the toward focus direction.

In a specific embodiment wherein the edge phantom has at least one flat lateral face the beveling of at least one of the lateral faces of the phantom is directed in a way such that a plane comprising said beveled lateral face also comprises the focus of the source of radiation.

For example, in case of an edge phantom comprising three lateral faces (edge planes) used for system sharpness analysis in three different spatial directions, the focus point of the source of radiation is the top of a pyramid the faces of which comprise the lateral faces of the phantom.

According to the present invention at least one lateral face is beveled.

However, more than one edge plane may be beveled.

In general, if all curved or flat lateral edge-faces of the phantom are directed such that each of them comprises a straight line, through any point on the lateral face, containing the focus of the radiation source, the focus point of said x-ray source will thus be the top of a three-dimensional geometric shape the envelope of which comprises all edge faces of the phantom.

Under these geometrical conditions direct rays emitted by the source of radiation will be tangential to the edge faces of the edge phantom in nominal position and the sharpness measurement will no longer be disturbed by undesired semi-shadow effects at the absorber's edges.

The use of an edge phantom comprising at least two plane edge faces provides that only a single exposure is required for generating a radiation image of the edge phantom by means of which the sharpness of the radiation image recording and detection system in two different spatial directions can be evaluated.

On and off edge sharpness analysis can be supported in case the phantom has four edges.

In case of a radiation image recording and detection system based on photo-stimulate phosphor technology as described higher, the sharpness of the system in the fast scan direction (line scanning direction) as well as in the slow scan direction (transport direction) can be measured by means of a single exposure of the phantom.

The present invention is suitable for single and composed, flat or curved edge features and patterns and applicable to any type of absorber medium and shape.

The edge phantom may be part of a larger phantom comprising features that are engineered for the purpose of other types of measurement. The edge phantom may have different forms such as a polygon (triangle, rectangle, square, . . . ) or circular, ellipse, any free form etc.

BRIEF DESCRIPTION OF THE DRAWINGS

Specific embodiments of edge phantoms according to the present invention as well as the method of the present invention will be described hereafter with reference to the following drawings in which FIG. 1 schematically illustrates a method of assessing the step response based sharpness of a radiation recording and detection system of the above-described kind.

DETAILED DESCRIPTION OF THE INVENTION

Figure 1:
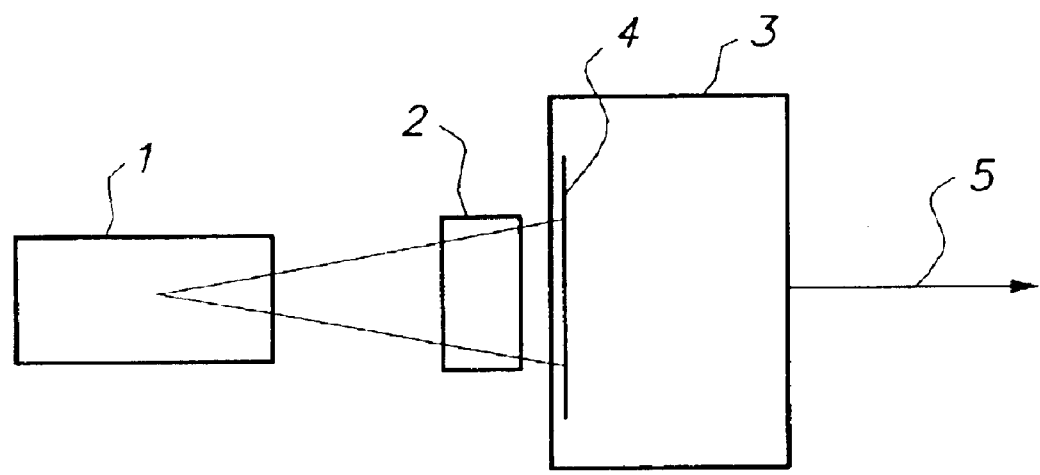

FIG. 1 schematically illustrates the method of the present invention.

An edge phantom (2) is, exposed to radiation emitted by a source of radiation (1). The exposure is generally performed under predefined exposure conditions such as X-ray spectrum, irradiation level and distance from source to detector surface etc.

The radiation image of the phantom is recorded by a radiation image recording and detection system (3). Such a system is for example a digital radiography system based on temporary recording of the radiation image on a photo-stimulate phosphor (4) as described higher.

The radiation image recording and detection system (3) generates a digital signal representation (5) representative of the radiation image of the phantom. This digital image can then be evaluated.

In one embodiment the radiation image is recorded on a photo-stimulate phosphor screen and the recorded radiation image is detected by two-dimensionally scanning said screen with stimulating radiation so as to emit image-wise modulated light.

The two-dimensional scanning is e.g. obtained by linewise scanning the phosphor screen with a laser beam or by means of a linear source of illumination (fast scan direction) and by transporting the screen in a direction perpendicular to the fast scan direction. (i.e. slow scan direction).

The image-wise modulated light is then detected, e.g. By means of a photo-multiplier or a solid state detector assembly and converted into a digital signal representation.

In such a system it is advantageous to use an edge phantom which comprises two lateral faces each lying in a plane comprising the focus (8) of said source of radiation (1).

If each of said lateral faces is positioned approximately parallel with one of the scanning directions of the two-dimensional scanning, the step response and sharpness of the system in both scanning directions can be calculated from a single exposure digital signal representation.

In a specific embodiment a rectangular phantom was positioned perpendicular to the optical axis of the radiation source and centered relative to the optical axis of the source.

The distance between the focus of the source of radiation and the recording material was 1.5 m. The slope of the slanted edge relative to the optical axis was about 1 degree.

Figure 2:
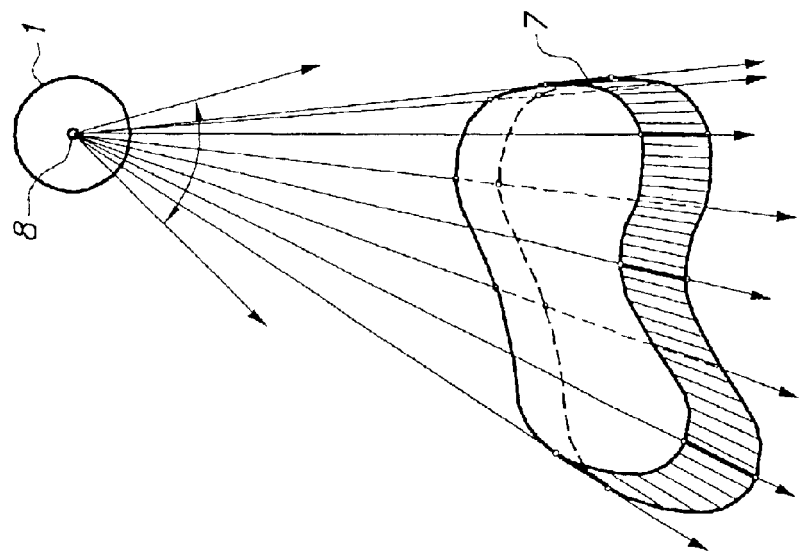

FIG. 2 shows an example of an edge phantom (2) according to the present invention.

The edge phantom consists of radiation attenuating material and has a three dimensional arbitrary shape.

The edge phantom has a lateral face (7). The curved lateral face (7) contains straight lines each comprising the focus point (8) of a source of radiation (1).

Figure 3:
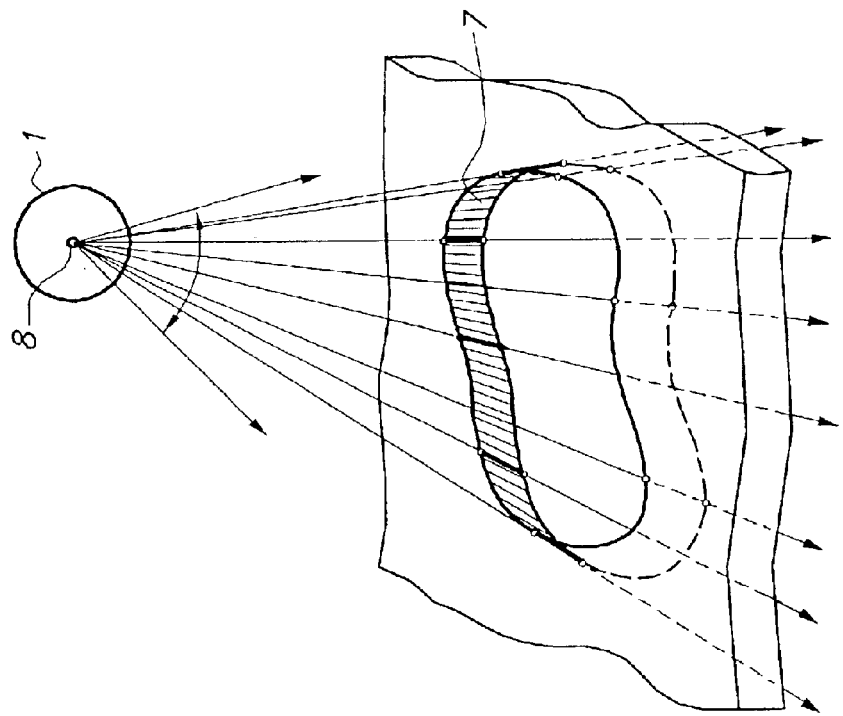
FIGS. 2–5 are embodiments of edge phantoms according to the present invention.

FIG. 3 shows an alternative embodiment of an edge phantom (2) according to the present invention.

The edge phantom consists of a piece of radiation attenuating material and has a cut away (9) of arbitrary shape.

The lateral face of the cut away is beveled in a direction so that the curved lateral face contains straight lines each comprising the focus point (8) of a source of radiation (1).

Figure 4:
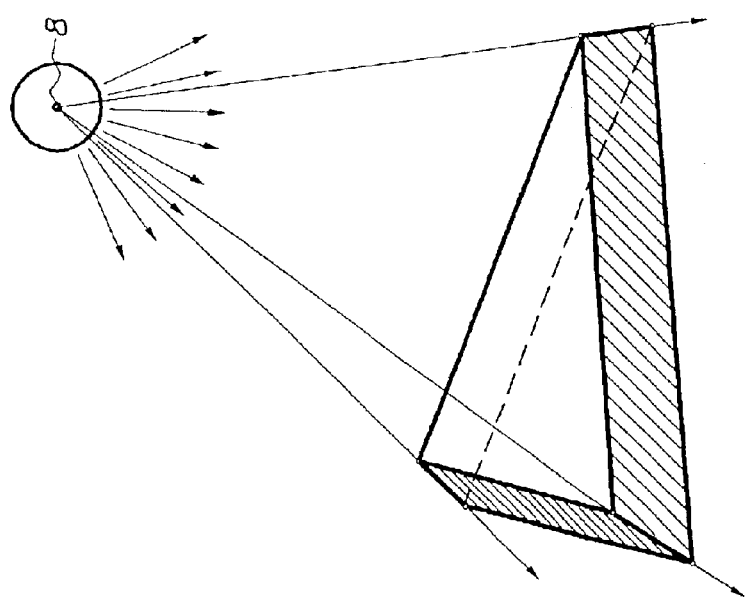

FIG. 4 shows an embodiment of an edge phantom having a triangular shape. The lateral, flat edge-faces are part of different planes each comprising the focus point of the radiation source.

Figure 5:
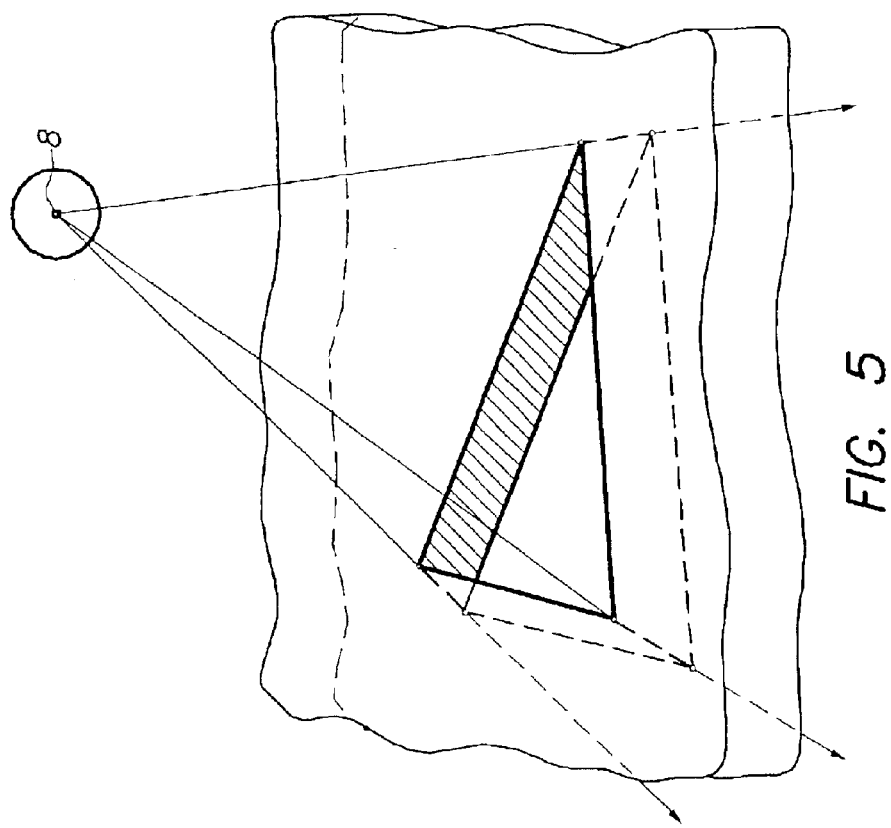

FIG. 5 shows another embodiment of an edge phantom. The edge phantom has a cut away of triangular shape. The lateral, flat edge faces are part of different planes each comprising the focus point of the radiation source.

What is claimed is:

1. An edge phantom for assessing the sharpness of a radiation image recording and detection system wherein said edge phantom is subjected to radiation to generate a radiation image of said phantom and wherein a digital image representation corresponding with said radiation image is generated and evaluated, wherein any line, outside a plane perpendicular to a top face of the edge phantom, connecting a focus of a source of radiation with a point on a curved or flat lateral face, used for sharpness analysis, of said phantom coincides with a line part of the lateral face containing said point.

2. An edge phantom according to claim 1 wherein at least one lateral face of said edge phantom lies in a plane comprising the focus of said source of radiation.

3. An edge phantom according to claim 1 wherein said edge phantom comprises two lateral faces each lying in a plane comprising the focus of said source of radiation.

4. An edge phantom according to claim 1 wherein said edge phantom comprises four lateral faces each lying in a plane comprising the focus of said source of radiation.

5. A method of assessing the sharpness of a radiation image recording and detection system comprising the steps of exposing an edge phantom to an amount of radiation emitted by a source of radiation under pre-defined exposure conditions, thereby generating a radiation image of said edge phantom, recording said radiation image, detecting the recorded radiation image and generating a digital image representation corresponding with the detected radiation image, evaluating said digital image representation characterized in that any line, outside a plane perpendicular to the top face of the edge phantom, connecting the focus of said source of radiation with a point on a curved or flat lateral face, used for sharpness analysis, of said phantom, coincides with a line part of said lateral face containing said point.

6. A method according to claim 5 wherein at least one lateral face of said edge phantom lies in a plane comprising the focus of said source of radiation.

7. A method according to claim 5 wherein said edge phantom comprises two lateral faces each lying in a plane comprising the focus of said source of radiation.

8. A method according to claim 5 wherein said edge phantom comprises four lateral faces each lying in a plane comprising the focus of said source of radiation.

9. A method according to claim 5 wherein said radiation image is recorded on a photo-stimulate phosphor screen and wherein the recorded radiation image is detected by two-dimensionally scanning said screen with stimulating radiation so as to emit image-wise modulated light and wherein said image-wise modulated light is detected and converted into a digital signal representation.

10. A method according to claim 5 wherein each of said lateral faces is positioned substantially parallel with one of the scanning directions of the two-dimensional scanning.

* * * * *